United States Patent

Bahrmann et al.

[11] Patent Number: 5,932,770
[45] Date of Patent: *Aug. 3, 1999

[54] PROCESS FOR RECOVERY OF PHOSPHINE OXIDES AND ALKLYLSARYLPHOSPHINES FROM REACTION MIXTURES OF A HOMOGENEOUS HYDROFORMYLATION

[75] Inventors: Helmut Bahrmann, Hamminkeln; Thomas Müller, Dinslaken, both of Germany

[73] Assignee: Hoechst Aktiengesellschaft, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/909,234

[22] Filed: Aug. 11, 1997

[30] Foreign Application Priority Data

Aug. 13, 1996 [DE] Germany .......................... 196 32 530

[51] Int. Cl.$^6$ ...................................................... C07F 9/50
[52] U.S. Cl. .................................. 568/17; 568/13; 568/15
[58] Field of Search ................................. 568/13, 14, 15, 568/16, 17, 11, 429, 451

[56] References Cited

U.S. PATENT DOCUMENTS

| | | | |
|---|---|---|---|
| 4,740,626 | 4/1988 | Bahrmann | 568/454 |
| 5,395,979 | 3/1995 | Deckman | 568/454 |
| 5,741,941 | 4/1998 | Bahrmann | 568/451 |

FOREIGN PATENT DOCUMENTS

| | | |
|---|---|---|
| 0216315 | 4/1987 | European Pat. Off. . |
| 2045169 | 3/1972 | Germany . |
| 2074166 | 10/1981 | United Kingdom . |

OTHER PUBLICATIONS

CA:106:186370 abs of JP61120167 Jun. 1986.
Hawley's "condenser chem dictionary" 12ed p. 856 1993.

*Primary Examiner*—Gary Geist
*Assistant Examiner*—Jean F Vollano
*Attorney, Agent, or Firm*—Bierman, Muserlian and Lucas

[57] ABSTRACT

A process for separating off phosphine oxides and alkylarylphosphines from an organic reaction mixture of a homogeneous hydroformylation carried out with the use of a catalyst system, which reaction mixture contains organometallic complex compounds and, in a molar excess, ammonium salts of aromatic phosphines as ligands comprising subjecting the organic reaction mixture to an extraction treatment with a 0.001–0.5% strength by weight of an alkali metal hydroxide or alkaline earth metal hydroxide solution and separating off the aqueous phase containing the phosphine oxides and alkylarylphosphines to decrease markedly the concentration of the phosphine oxides and alkylarylphosphines in the hydroformylation mixture, which process is particularly suitable for continuously operated hydroformylations.

8 Claims, No Drawings

PROCESS FOR RECOVERY OF PHOSPHINE OXIDES AND ALKLYLSARYLPHOSPHINES FROM REACTION MIXTURES OF A HOMOGENEOUS HYDROFORMYLATION

FIELD OF THE INVENTION

The invention relates to a process for recovering phosphine oxides and alkylarylphosphines from reaction mixtures of a homogeneous hydroformylation.

STATE OF THE ART

The hydroformylation of olefins which is carried out on a large scale industrially is increasingly being performed in the presence of catalyst systems based on rhodium-complex compounds which contain tertiary phosphines or phosphites as ligands. Since the ligands are generally present in excess, the catalyst system comprises organometallic compounds and additional pure ligand. In accordance with the solubility of these catalyst systems in organic media, the hydroformylation is performed in an homogeneous phase.

To separate off the reaction product and recover the catalyst system homogeneously dissolved in the reaction mixture, the reaction product is generally distilled off from the reaction mixture. However, because of the thermal sensitivity of the aldehydes formed, this is only possible in the hydroformylation of lower olefins having up to about 8 carbon atoms in the molecule. In the hydroformylation of long-chain olefins or olefinic compounds having functional groups, thermally sensitive products or products having a high boiling point are formed which can no longer be separated from the catalyst satisfactorily by distillation. The thermal stress of the distillation material leads, as a result of thick oil formation, to considerable losses of valuable product and, as a result of decomposition of the complex compounds, to losses of catalyst. This critically decreases the economic attraction of the process.

To avoid recovery of the catalyst system by a thermal route, various process alternatives have been developed. EP-A-0 216 375 discloses a process for preparing aldehydes by reacting olefins with hydrogen and carbon monoxide in an homogeneous phase in the presence of a catalyst system containing rhodium and aromatic phosphines in a molar excess as ligands, wherein the aromatic phosphines used are the ammonium salts of sulfonated or carboxylated triarylphosphines which are soluble in organic media and insoluble in water.

The ammonium ions have the formulae $(NR_2H_2)^+$ and/or $(NR_3H)^+$, where R is an alkyl of 4 to 12 carbon atoms or an aryl or cycloalkyl of 6 to 12 carbon atoms.

To recover the catalyst system from the reaction product, the hydroformylation mixture in this case is first treated with a base, e.g. alkali metal hydroxide or alkaline earth metal hydroxide solutions. During this, the corresponding secondary or tertiary amines are released from the $(NR_2H_2)^+$ or $(NR_3H)^+$ salts, and, at the same time, a water-soluble alkali metal salt or alkaline earth metal salt of the sulfonated or carboxylated triarylphosphine is formed, which as a result passes into the aqueous phase and, together with the complex on phosphorus-bound rhodium, can be separated from the organic phase containing the hydroformylation product via an extraction.

A further possibility for separating off the catalyst system of an homogeneous hydroformylation from the reaction mixture is disclosed by German patent application 196 19 527.6. The catalyst system used contains water-insoluble rhodium-complex compounds and, as ligands, ammonium salts of sulfonated, carboxylated or phosphonated aromatic disphosphines and is separated from the reaction mixture after the hydroformylation by membrane filtration on a semipermeable polyaramid membrane.

However, in the course of such homogeneous hydroformylation reactions, side reactions and degradation reactions occur on the catalyst system, particularly on the ligands. Oxidation of the phosphorus(III) in the respective ammonium salts of the aromatic phosphines forms phosphine oxides. In addition, in the course of the hydroformylation, alkylarylphosphines form from the aromatic phosphines, by aryls of the aromatic phosphines being exchanged for alkyls, the alkyls being derived from the olefin which is being hydroformylated. Both the phosphine oxides and the alkylaryl-phosphines are present in this case in the form of their ammonium salts.

Whereas the phosphine oxides can no longer participate in complex formation with the metal used, particularly rhodium, and thus lead to a gradual depletion of ligand in the catalyst system, the alkylarylphosphines are still capable of forming complexes. However, these complexes are not catalytically active, or are only slightly active, and thus have an activity-lowering effect on the hydroformylation. This formation of phosphine oxide and alkylarylphosphine poses a problem, especially when the hydroformylation is carried out continuously or the same catalyst solution is used repeatedly and the phosphine oxides and alkylarylphosphines can thus continue to accumulate over a relatively long period.

OBJECTS OF THE INVENTION

It is an object of the invention to provide a process for removing the catalytically inactive phosphine oxides and deactivating alkylarylphosphines from the reaction mixture of a homogeneous hydroformylation, by which process the concentration of the phosphine oxides and alkylarylphosphines can be decreased in the hydroformylation reaction mixture.

This and other objects and advantages of the invention will become obvious from the following detailed description.

THE INVENTION

The process of the invention for recovering phosphine oxides and alkylarylphosphines from the organic reaction mixture of a homogeneous hydroformylation carried out with the use of a catalyst system, which reaction mixture contains organometallic complex compounds and, in a molar excess, ammonium salts of aromatic phosphines as ligands comprises subjecting the organic reaction mixture to an extraction with a 0.001–0.5% strength by weight of aqueous alkali metal hydroxide or alkaline earth metal hydroxide solution and then recovering the aqueous phase containing the phosphine oxides and alkylarylphosphines.

The alkali metal hydroxide or alkaline earth metal hydroxide solution used for the extraction is preferably sodium hydroxide solution or potassium hydroxide solution. The concentration of this aqueous alkali metal hydroxide or alkaline earth metal hydroxide solution is 0.001–0.5% by weight, preferably 0.01–0.05% by weight.

The organic reaction mixture to be subjected to the extraction originates from a homogeneous hydroformylation for preparing aldehydes by reacting olefinic compounds with hydrogen and carbon monoxide.

The catalyst system used in the hydroformylation contains organometallic complex compounds and, in a molar excess, ammonium salts of aromatic phosphines as ligands. These ammonium salts of aromatic phosphines are according to the invention ammonium salts of aromatic mono- or disphosphines.

The ammonium salts of aromatic monophosphines preferably used are alkylammonium and/or arylammonium salts of sulfonated or carboxylated triarylphosphines of the formula

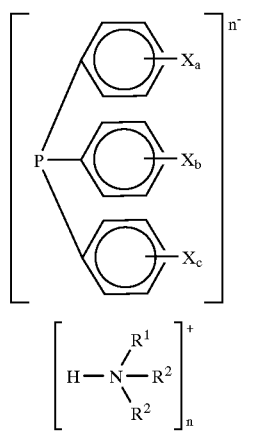

wherein X is sulfonate or carboxylate, a, b and c are individually 0 or 1, where at least one of a, b or c must be 1, n is 1, 2 or 3, $R^1$ and $R^2$ are individually alkyl of 4 to 30 carbon atoms or aryl of 6 to 10 carbon atoms or cycloalkyl of 6 to 10 carbon atoms and $R^1$ can also be hydrogen.

The homogeneous hydroformylation of olefins with the use of catalyst systems which contain as ligands, compounds of formula I, is described in German patent application submitted on the same day and in EP-A-0 216 375.

As further representatives of ammonium salts of aromatic monophosphines, compound of formula II are used

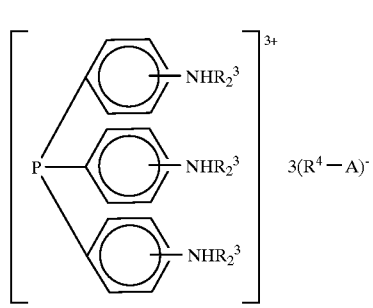

wherein $R^3$ is hydrogen or alkyl of 1 to 12 carbon atoms, $R^4$ is alkyl of 1 to 25 carbon atoms or aryl of 6 to 10 carbon atoms and A is sulfonate ($SO_3^-$) or carboxylate ($COO^-$) or phosphonate ($R-PO_3^{2-}$).

Representatives of the ammonium salts of aromatic diphosphines preferably used are compounds of the formula

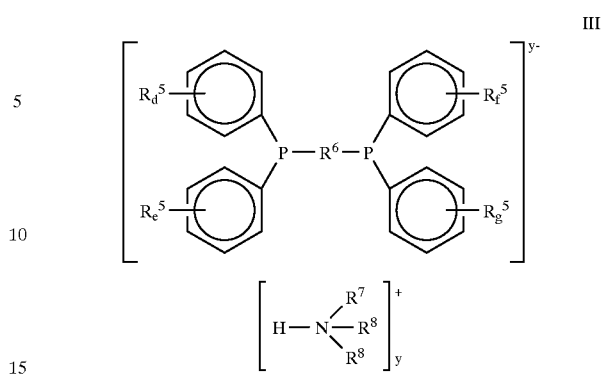

wherein $R^5$ is carboxylate ($COO^-$), sulfonate ($SO_3^-$), phosphonate ($PO_3^{2-}$) or 2-aminoethanebisphosphonate [NH—$CH_2$—$CH(PO_3^{2-})_2$], $R^6$ is linear alkylene of 1 to 8 carbon atoms, oxygen-containing alkylene of 2 to 6 carbon atoms, cycloalkylene of 3 to 10 carbon atoms or formulae IV, V, VI or VII.

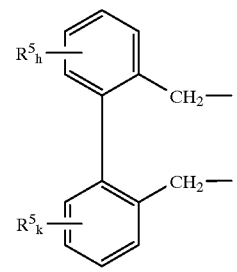

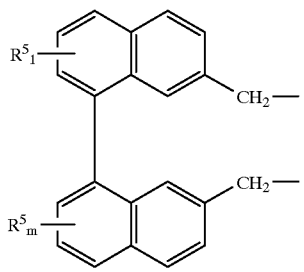

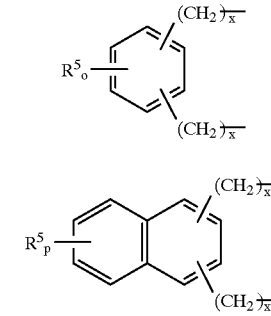

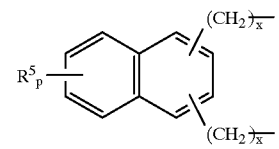

d, e, f, g, h, k, l, m, o and p are individually 0 or 1, where at least one of d, e, f, g, h, k, l, m, o or p must be 1, y is the sum of d, e, f, g, h, k, l, m, o and p, x are individually 0 or 1, $R^7$ and $R^8$ are individually alkyl of 4 to 26 carbon atoms, substituted or unsubstituted aryl of 6 to 10 carbon atoms or cycloalkyl of 6 to 10 carbon atoms or benzyl and $R^7$ can also be hydrogen.

The homogeneous hydroformylation of olefins with the use of catalyst systems, which contain as ligands, compounds of formula III is described in German patent application Serial No. 196 19 527.6.

In addition, as ammonium salts of aromatic diphosphines, compounds of the following formula have proved to be useful

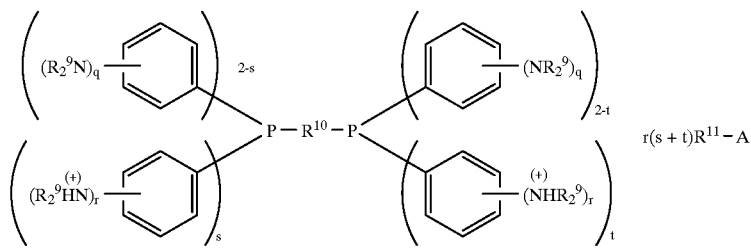

VIII wherein $R^9$ is hydrogen or alkyl of 1 to 12 carbon atoms, $R^{10}$ is linear alkylene of 1 to 8 carbon atoms, oxygen-containing alkylene of 2 to 4 carbon atoms, cycloalkylene of 3 to 10 carbon atoms or the formulae

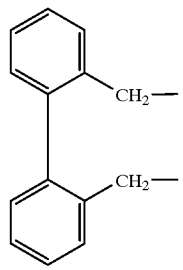

IX

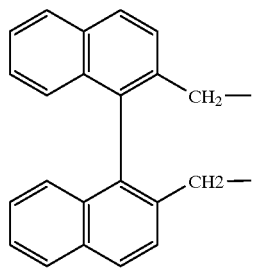

X $R^{11}$ is alkyl of 1 to 25 carbon atoms or aryl of 6 to 10 carbon atoms, A is a carboxylate ($COO^-$) or sulfonate ($SO_3^-$) and q is 0, r is 1, s is 1 and t is 1, or q is 1, r is 1, s is 1 or 2 and t is 1 or 2, or, if $R^{10}$ is formula IX or X, q is 1, r is 0, s is 0 or 1 and t is 0 or 1.

The homogeneous hydroformylation of olefins with the use of catalyst systems, which contain as ligands, compounds of formula VIII is described in German patent application Serial No. 196 09 337.6.

In the context of the homogeneous hydroformylation, it is not necessary to use the ammonium salts of the aromatic phosphines of formulae I, II, III and VIII as uniform compounds in the catalyst system. For example, different sulfonation states of the phosphines and/or sulfonate mixtures having different ammonium cations can also be reacted.

In the hydroformylation, olefinically unsaturated compounds of 2 to 30 carbon atoms are used which can have one or more double bonds. Suitable compounds are substituted or unsubstituted alkenes of 6 to 30 carbon atoms, substituted or unsubstituted dienes of 4 to 10 carbon atoms, substituted or unsubstituted cycloalkenes or dicycloalkenes of 5 to 12 carbon atoms in the ring system, esters of an unsaturated carboxylic acid of 3 to 20 carbon atoms and of an aliphatic alcohol of 1 to 18 carbon atoms, esters of a saturated carboxylic acid of 2 to 20 carbon atoms, and an unsaturated alcohol of 2 to 18 carbon atoms, unsaturated alcohols or ethers of 3 to 20 carbon atoms or araliphatic olefins of 8 to 20 carbon atoms.

The substituted or unsubstituted alkenes of 6 to 30 carbon atoms can be linear or branched alkenes having a terminal or internal position of the double bond. Preference is given to linear olefins of 6 to 18 carbon atoms such as n-hex-1-ene, n-hept-1-ene, n-oct-1-ene, n-non-1-ene, n-dec-1-ene, n-undec-1-ene, n-dodec-1-ene, n-octadec-1-ene and acyclic terpenes. Suitable compounds are also branched alkenes such as diisobutylene (2,4,4-trimethylpent-1-ene), tripropylene, tetrapropylene and dimersol (dibutylene).

Preferred examples of unsubstituted dienes of 4 to 10 carbon atoms are 1,3-butadiene, 1,5-hexadiene and 1,9-decadiene.

Examples of substituted and unsubstituted cycloalkenes or dicycloalkenes of 5 to 12 carbon atoms in the ring system are cyclohexene, cyclooctene, cyclooctadiene, dicyclopentadiene and cyclic terpenes such as limonene, pinene, camphorene and bisabolene. Preference is given to dicyclopentadiene. An example of araliphatic olefins of 8 to 20 carbon atoms is styrene.

Examples of esters of an unsaturated carboxylic acid of 3 to 20 carbon atoms and an aliphatic alcohol of 1 to 18 carbon atoms are acrylates and methacrylates of 1 to 18 carbon atoms in the alcohol component.

The esters of a saturated carboxylic acid of 2 to 20 carbon atoms and an unsaturated alcohol of 2 to 18 carbon atoms include the vinyl and allyl esters of 2 to 20 carbon atoms in the carboxylic acid component, for example vinyl acetate.

The unsaturated alcohols and ethers include, for example, allyl alcohols and vinyl ethers.

The phosphine oxide formed in the course of the hydroformylation by oxidation of the phosphorus(III) in the ammonium salts of the aromatic phosphines, and the alkylaryl-phosphines which are also formed, are present as ammonium salts. These ammonium salts, upon addition of the aqueous alkali metal hydroxide or alkaline earth metal hydroxide solution, are converted into the corresponding alkali metal salts or alkaline earth metal salts, which are water soluble and therefore pass into the aqueous phase.

It is of essential importance in this case that the alkali metal hydroxide or alkaline earth metal hydroxide solution used for the extraction has a concentration in the range of 0.001 to 0.5% by weight. Only by keeping within this range can the ligands themselves, i.e. the ammonium salts of the aromatic phosphines, be prevented from passing at a relatively high level into the aqueous phase and, in addition, base-catalyzed secondary reactions, such as the aldolization of the aldehydes formed, do not occur. It has further proved useful to carry out the extraction at as low as possible a pH of the organic reaction mixture. Particular preference is given to a pH of 2.5 to 4.0, preferably 2.8 to 3.6.

During the extraction of the reaction mixture from a homogeneous hydroformylation, in addition to the alkali metal salts or alkaline earth metal salts of the phosphine oxides or alkylarylphosphines, amine is also released in a corresponding amount, which accumulates in the catalyst solution, but does not have any adverse effect on the latter. By adding an appropriate amount of fresh phosphines, the respective alkylammonium and/or arylammonium salts of formulae I, II, III and VIII can be regenerated. The phosphines can be added either simultaneously with the alkali metal hydroxide or alkaline earth metal hydroxide solution, or not until after the extraction.

The process according to the invention can be carried out in the following manner. The organic reaction mixture formed in the homogeneous hydroformylation is removed from the reactor and contains the aldehydes formed, unreacted olefins, the catalyst system of organometallic complex compound and the ammonium salts of the aromatic phosphines, as well as the phosphine oxides and alkylarylphosphines to be removed, and possibly other decomposition products and by-products. This reaction mixture is depressurized once or repeatedly to remove unreacted synthesis gas as off-gas. It has proved to be useful in this case to add the alkali metal hydroxide or alkaline earth metal hydroxide solutions to be used for the extraction to the hydroformylation reaction mixture prior to the depressurization to exploit the mixing effect occurring during the depressurization.

The aqueous phase containing the phosphine oxides and alkylarylphosphines is separated following the depressurization using a conventional phase separator. This extraction step can be carried out repeatedly in series but it is also possible not to carry out the extraction of the phosphine oxides and alkylarylphosphines until after the depressurization in known extraction apparatuses, such as mixer-settler batteries. The extraction can be performed at an elevated temperature of 50 to 90° C. or at room temperature. The organic reaction mixture remaining after separating the aqueous phase is then preferably subjected to a membrane filtration, the catalyst system being separated off from the hydroformylation product.

The process of the invention enables the concentration of the phosphine oxides and the alkylarylphosphines in the organic reaction mixture of a homogeneous hydroformylation to be markedly reduced. Preferably, the process is applied to reaction mixtures of continuously operated homogeneous hydroformylations. Even by a simple extraction, an amount of phosphine oxides and alkylarylphosphines can be separated from the hydroformylation reaction mixture which far exceeds the amount of these decomposition products formed in each pass through the continuous reaction.

By repeated extraction, the phosphine oxides and alkyldiaryl-phosphines can be separated to a still greater extent. However, in most cases, it is already sufficient merely to subject a part-stream of the hydroformylation reaction mixture to the above-described extraction, or to operate the extraction only at intervals.

In the following examples, there are described several preferred embodiments to illustrate the invention. However, it should be understood that the invention is not intended to be limited to the specific embodiments.

EXAMPLES

The following abbreviations are used:
TPPOTS: Triphenylphosphine oxide trisulfonate
TPPODS: Triphenylphosphine oxide disulfonate
PDSPP: Propyldisulfophenylphosphine
TPPTS: Triphenylphosphine trisulfonate
TPPDS: Triphenylphosphine disulfonate
BSNS: Sodium benzenesulfonate Example 1

A reaction mixture from the hydroformylation of propylene using a catalyst system of rhodium-complex compounds and the distearylammonium salt of TPPTS as ligand contained 46.98 mmol of phosphorus(III)/kg and 10.81 mmol of phosphorus(V)/kg. 148 g of such a reaction mixture (6.86 mmol of phosphorus(III) and 1.58 mmol of phosphorus (V)) were extracted at 70° C. with 10 ml of 0.05% strength by weight of sodium hydroxide solution for 15 minutes. After phase separation for 10 minutes, 9.28 g of the aqueous phase were separated and analyzed by HPLC. The amounts of substances shown in Table 1 were determined.

TABLE 1

| Substance extracted | mmol in the aqueous phase | % of amount used |
|---|---|---|
| TPPOTS | 0.052 | 3.29 |
| TPPODS | 0.004 | 0.25 |
| PDSPP | $0.4 \cdot 10^{-4}$ | 0.03 |
| TPPTS | $8.7 \cdot 10^{-4}$ | 0.01 |
| TPPDS | $6.2 \cdot 10^{-4}$ | 0.01 |

It can be seen from Table 1 that even a single extraction operation can remove 3.29% of the TPPOTS present in the reaction mixture and 0.25% of the TPPODS. This was already considerably more than the order of magnitude of that newly formed in the context of one pass through the continuous hydroformylation. By repeating the extraction steps several times, the amount of phosphine oxides extracted was increased correspondingly.

Example 2

Hydroformylation of dicyclopentadiene in toluene using a catalyst system of rhodium-complex compounds and the distearylammonium salt of TPPTS as ligand in a molar excess (21 ppm rhodium, phosphorus:rhodium ratio=50, toluene content 60% by weight) gave a reaction mixture having a phosphorus(III) concentration of 11.9 mmol/kg and a phosphorus(V) concentration of 11.9 mmol/kg. 207 g of this reaction mixture were subjected to an extraction with a 0.04% strength sodium hydroxide solution at 70° C. for 60 minutes. After phase separation for 5 minutes, the aqueous phase was separated and the phosphorus(V) concentrations of TPPDS and TPPOTS were analyzed by HPLC. The phosphorus(III) concentration was determined by titrimetry and the amounts of substances extracted shown in Table 2 were determined.

The separated organic phase was admixed with 1.53 ml of a 5% strength sodium hydroxide solution and then extracted again with 206.1 g of a 0.04% strength sodium hydroxide solution under similar conditions as described above. The aqueous phase, after phase separation, was analyzed as described.

The organic phase was extracted two further times, likewise as described and the results are summarized in Table 2.

TABLE 2

| Number of extraction stages | Substances extracted [% by weight, based on the amounts of the individual substance present in the reaction mixture used for the extraction] | | | |
|---|---|---|---|---|
| | TPPTS | TPPODS | TPPOTS | BSNS |
| 1 | — | 17 | 31 | 21 |
| 2 | 1.2 | 26 | 56 | 29 |
| 3 | 3.3 | 40 | 80 | 29 |
| 4 | 10.7 | 62 | 98 | 36 |

Various modifications of the process of the invention may be made without departing from the spirit or scope thereof and it is to be understood that the invention is intended to be limited only as defined in the appended claims.

What we claim is:

1. A process for recovering triaryl phosphine oxides and alkylarylphosphines from an organic reaction mixture of a homogeneous hydroformylation carried out with the use of a catalyst system, which reaction mixture contains organophosphine complex compounds and, in a molar excess, ammonium salts of aromatic phosphines as ligands, comprising subjecting the organic reaction mixture to an extraction with a 0.001–0.5% strength by weight of an alkali metal hydroxide or alkaline earth metal hydroxide solution at a pH of 2.5 to 4.0 and recovering the aqueous phase containing the triaryl phosphine oxides and alkylarylphospines.

2. The process of claim 1, wherein the alkali metal hydroxide solution used is a sodium hydroxide solution or potassium hydroxide solution.

3. The process of claim 1, wherein the concentration of the alkali metal hydroxide or alkaline earth metal hydroxide solution is 0.01–0.05% by weight.

4. The process of claim 1 wherein the ammonium salts of the aromatic phosphines are ammonium salts of aromatic mono- or diphosphines.

5. The process of claim 4, wherein the ammonium salts of aromatic monophosphines used are at least one member of the group consisting of alkylammonium and arylammonium salts of sulfonated and carboxylated triarylphosphines of the formula

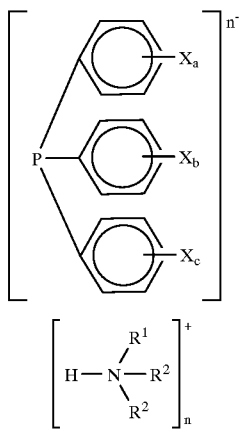

I wherein X is sulfonate ($SO_3^-$) or carboxylate ($COO^-$) a, b and c are individually 0 or 1, and at least one of a, b or c must be 1, n is 1, 2 or 3, $R^1$ and $R^2$ are individually selected from the group consisting of alkyl of 4 to 30 carbon atoms, aryl of 6 to 10 carbon atoms, and cycloalkyl of 6 to 10 carbon atoms and $R^1$ can also be hydrogen.

6. The process of claim 4, wherein the ammonium salts of aromatic monophosphines used are compounds of the formula

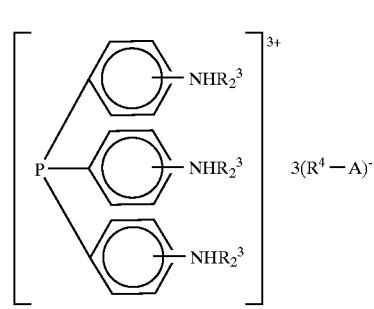

II wherein $R^3$ is hydrogen or alkyl of 1 to 12 carbon atoms, $R^4$ is alkyl of 1 to 25 carbon atoms or aryl of 6 to 10 carbon atoms and A is sulfonate, ($SO_3^-$) or carboxylate ($COO^-$) or phosphonate ($R—PO_3^{2-}$).

7. The process of claim 4, wherein the ammonium salts of aromatic diphosphines used are compounds of the formula

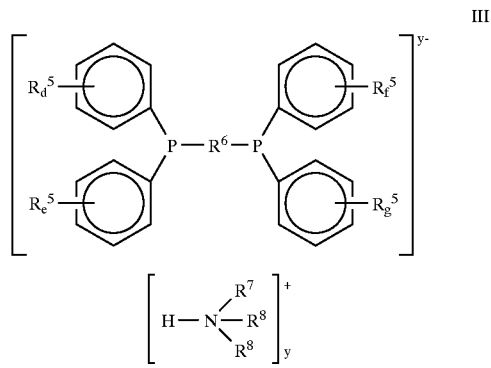

III wherein $R^5$ is carboxylate ($COO^-$), sulfonate ($SO_3^-$), phosphonate ($PO_3^{2-}$) or 2-aminoethanebisphosphonate [$—NH—CH_2—CH(PO_3^{2-})_2$], $R^6$ is selected from the group consisting of a linear alkylene of 1 to 8 carbon atoms, an oxygen-containing alkylene of 2 to 6 carbon atoms, cycloalkylene of 3 to 10 carbon atoms and a formula

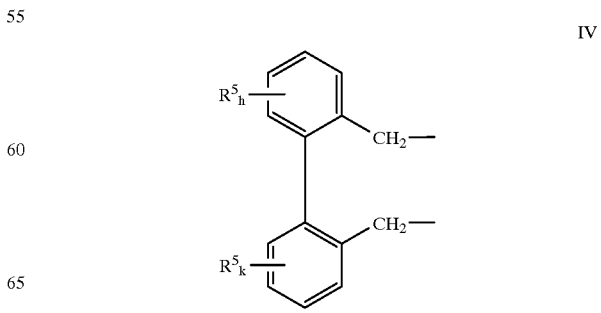

IV

-continued

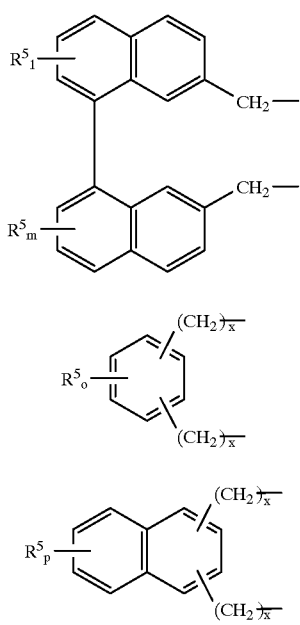

V

VI

VII

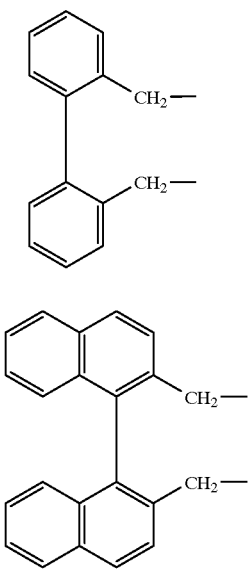

IX

X d, e, f, g, h, k, l, m, o and p are individually 0 or 1, with at least one of d, e, f, g, h, k, l, m, o or p being 1, y is the sum of d, e, f, g, h, k, l, m, o and p, x are individually 0 or 1, $R^7$ and $R^8$ are individually selected from the group consisting of alkyl of 4 to 26 carbon atoms, optionally substituted aryl of 6 to 10 carbon atoms, cycloalkyl of 6 to 10 carbon atoms and benzyl and $R^7$ can also e hydrogen.

8. process of claim 4, wherein the ammonium salts of aromatic diphosphines used are compounds of the formula

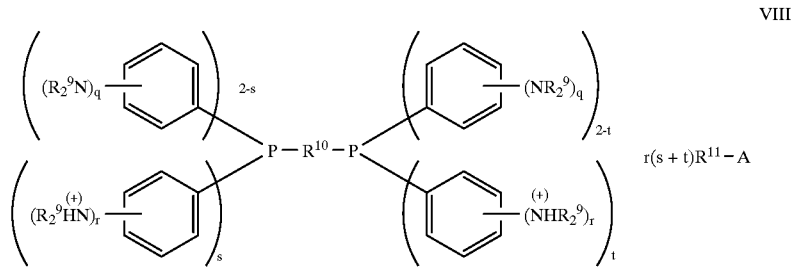

VIII wherein $R^9$ is hydrogen or alkyl of 1 to 12 carbon atoms, $R^{10}$ is selected from the group consisting of linear alkylene of 1 to 8 carbon atoms, oxygen-containing alkylene of 2 to 4 carbon atoms, of the formula and cycloalkylene of 3 to 10 carbon atoms, $R^{11}$ is alkyl of 1 to 25 carbon atoms or aryl of 6 to 10 carbon atoms, A is carboxylate (COO$^-$) or sulfonate (SO$_3$) and q is 0, r is 1, s is 1 and t is 1, or q is 1, r is 1, s is 1 or 2 and t is 1 or 2, or, if $R^{10}$ is formula IX or X, q is 1, r is 0, s is 0 or 1 and t is 0 or 1.

\* \* \* \* \*